(12) United States Patent
Young (10) Patent No.: US 6,565,520 B1
(45) Date of Patent: May 20, 2003

(54) APPARATUS FOR ULTRASONIC THERAPEUTIC TREATMENT

(75) Inventor: Michael John Radley Young, Ashburton (GB)

(73) Assignee: Orthosonics Ltd., Ashburton South Devon (GB)

( * ) Notice: Subject to any disclaimer, the term of this patent is extended or adjusted under 35 U.S.C. 154(b) by 0 days.

(21) Appl. No.: 09/255,664

(22) Filed: Feb. 23, 1999

Related U.S. Application Data (63) Continuation-in-part of application No. PCT/GB97/02200, filed on Aug. 18, 1997.

(51) Int. Cl.⁷ ............................................. A61N 7/00
(52) U.S. Cl. ......................................................... 601/2
(58) Field of Search .......................... 601/1–4, 46, 80, 601/81; 600/439; 604/22

(56) References Cited

U.S. PATENT DOCUMENTS

| | | | | |
|---|---|---|---|---|
| 4,960,107 A | * | 10/1990 | Aida et al. .................. | 128/24 |
| 5,443,069 A | * | 8/1995 | Schaetzle ............... | 128/660.03 |
| 5,549,544 A | * | 8/1996 | Young et al. .................. | 601/2 |
| 5,618,275 A | * | 4/1997 | Bock .......................... | 604/290 |
| 5,827,204 A | * | 10/1998 | Grandia et al. ................ | 601/2 |
| 6,190,336 B1 | * | 2/2001 | Duarte et al. .................. | 601/2 |

* cited by examiner

Primary Examiner—Marvin M. Lateef
Assistant Examiner—Eleni Mantis Mercader
(74) Attorney, Agent, or Firm—Roy C. Hopgood (57) ABSTRACT

The method and apparatus of the invention are directed to surgically non-invasively treating skeleto/muscular injuries or of diagnosing bone fractures, involving application of two components of ultrasonic energy, to an external surface of living tissue, wherein the two components are of different frequencies in the range between 10 kHz and 4 MHz, and wherein separate transducers, each uniquely supplied with an excitation signal at a different one of the same two frequencies, are directionally disposed for acoustic propagation on the same directional axis.

24 Claims, 5 Drawing Sheets

APPARATUS FOR ULTRASONIC THERAPEUTIC TREATMENT

RELATED CASE

This application is a continuation-in-part of pending application PCT/GB97/02200, filed Aug. 18, 1997, said PCT application having an International Publication Date of Feb. 26, 1998 and being further identified as Publication No. WO 98/07470.

BACKGROUND OF THE INVENTION

The present invention relates to an improved medical appliance for ultrasonic therapeutic treatment and/or other operation upon living body tissue.

The application of ultrasound in diagnostic scanning techniques and therapeutic treatment of specific medical conditions has been widely reported in the technical literature over the last 20 to 30 years. However, prior to application GB 2274996A, which does disclose treatment apparatus operating in the kHz band, no relevant reference was found, for the use of frequencies in the range 30 to 100 kHz.

It is known that ultrasound therapeutic radiation in the MHz band has beneficial effects when treating soft-tissue injuries, and that such emissions are absorbed (attenuated) to differing degrees in different types of living tissue.

This characteristic of absorption or attenuation limits to some extent the scope for treating certain types of injury since in order to transmit adequate intensities of radiation to a deep injury, potentially harmful levels would have to be introduced into the outer tissue layers. To overcome this problem of natural attenuation at greater depth of injury, it has previously been proposed to use long-wave radiation in the 45 to 50 kHz band, with correspondingly improved transmission characteristics. This is described in U.S. Pat. No. 5,549,544, the disclosure of which is hereby incorporated by reference. It suffices here to note that said disclosure pertains to the use of a single excitation frequency in the range 20 to 120 kHz and to the employment of a body-contacting application head having a specific impedance (W) that closely matches that of human soft tissue.

The use of frequencies in the MHz band stems from the concept that therapeutic treatment using ultrasonic energy should be directed accurately to a well-defined region of tissue and that this is best achieved with a finely focused beam. However, it is often necessary to apply a broader range of treatment, and in this case, a mixture of comparatively higher and lower frequency vibrations is to be desired. For example, the characteristic wavelength corresponding to a 3 MHz transmission through soft tissue is about 0.5 mm; but at 40 kHz, the wavelength would be approximately 37.5 mm.

The combination of wavelengths, however achieved, will give a more even distribution of energy within the tissue being treated. Also, in cases where only local treatment, or treatment of an area close to the surface, is required, there is still a need for a treatment device which can selectively treat chosen areas.

However, since it is known that the attenuation of ultrasonic waves increases with increasing frequency, the general effect of high-frequency transmission is to produce relatively high energy-absorption rates close to the entry surface, and for the effect to fall off with increasing depth. It may therefore be concluded that, for a given power input, it is preferred to use a low-frequency input when treating deep-tissue injuries. This consideration becomes very important since in order to transmit enough energy to the required region, the risk of excessive absorption in surface layers may become unreasonably high when applying therapeutic ultrasound in the MHz band. For this reason, energy levels are limited by the requirement that intensity should not exceed 3 watts/cm$^2$.

Furthermore, conventional high frequency systems produce columnar (collimated) energy beams which can lead to a danger of standing waves, internal reflection and consequent hot spots in irradiated tissue. In contrast to this, longer wavelength transmissions exhibit a spherical wavefront, with diverse propagation characteristics and little or no risk of standing waves.

BRIEF STATEMENT OF THE INVENTION

It is an object of the present invention to provide improved ultrasonic means for combining benefits associated with long-wavelength treatment with those associated with shorter wavelength treatment.

According to one aspect of the present invention, apparatus is provided to treat muscular injuries within or below a body surface or to diagnose bone fractures, wherein the device comprises piezoelectric means to generate ultrasonic energy, said piezoelectric means comprising at least two generator means each adapted to deliver energy at a different frequency in the range 10 kHz to 4 MHz, a first application head adapted to be applied closely to the body surface and to deliver thereto energy from one of said generator means, and a second application head adapted to be applied closely to the body surface and to deliver energy thereto from another of said generator means.

Preferably, a first or low-frequency generator means provides energy at a frequency in the range of between, 10 to 110 kHz, advantageously 20 to 100 kHz and preferably in the region of 45 kHz.

Advantageously, a second or high-frequency generator means generates energy at a frequency in the region of 0.5 to 4 MHz, advantageously 0.5 to 3 MHz, and preferably in the region of 1 MHz.

In a preferred embodiment, the body-application heads for the respective generator means are adapted for location in spaced mutual adjacency at adjacent portions of a treatment surface of the apparatus, wherein the spacing provides an important degree of acoustic isolation between the respective heads.

At least the low-frequency application head may be machined or molded from a range of dense polymers including acetal, polypropylene and polycarbonate. These and similar materials all permit the transmission of low-amplitude ultrasound in the frequency range 30 to 100 kHz, with relatively low energy absorption. The head is machined from plastics material which is chosen because its specific impedance (W) closely matches that of human soft tissue.

As an example, acetal may be used, in which case applicable figures are:

$W_{acetal}=1.86\times10^6$ Kg M$^{-2}$sec$^{-1}$;

$W_{soft\ tissue}=1.65\times10^6$ kg M$^{-2}$sec$^{-1}$.

According to another aspect of the present invention, there is provided a method of treating muscular injuries or of diagnosing bone fractures, wherein the method comprises applying to an external surface of the tissue, two component sources of acoustic energy, each component having a different frequency in the range between 10 kHz and 4 MHz, and each component being applied independently to adjacent but separate portions of the external surface of a patient's body.

According to a further aspect of the invention, there is provided a surgically non-invasive method of treating deep-seated muscular injuries or of diagnosing bone fractures, wherein the method comprises the steps of applying to an external surface portion of the tissue an application head which comprises a first member capable of emitting acoustic energy, generally symmetrically about a directional axis and at a comparatively low frequency and independently applying acoustic energy at a relatively high frequency to an adjacent portion of the surface and with general symmetry about said axis.

DETAILED DESCRIPTION OF THE DRAWINGS

The invention will be described in detail for a preferred embodiment, in conjunction with the accompanying drawings, in which.

DETAILED DESCRIPTION OF A PREFERRED EMBODIMENT

Figure 1:
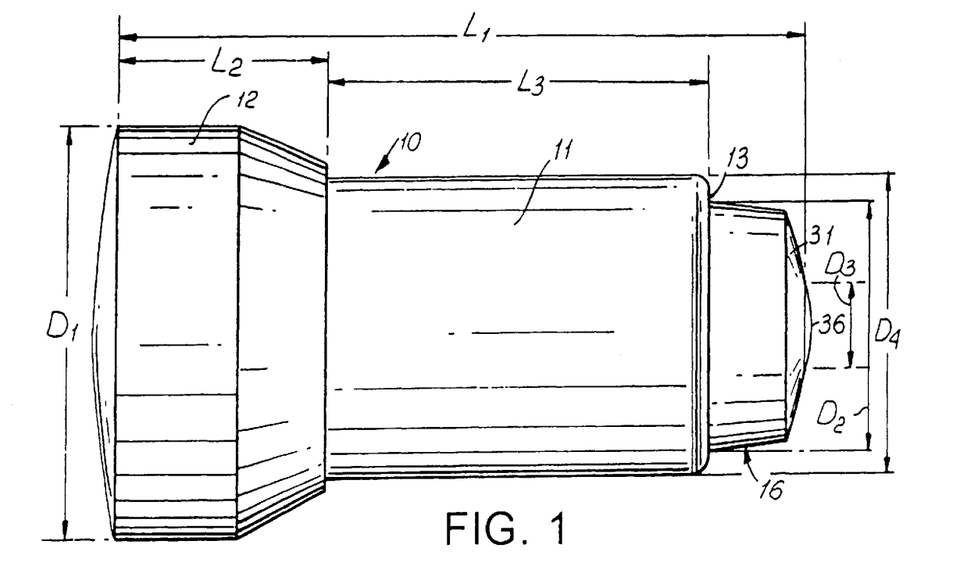
FIG. 1 is a view in side elevation of an ultrasonic therapeutic device of the invention.
Figure 2:
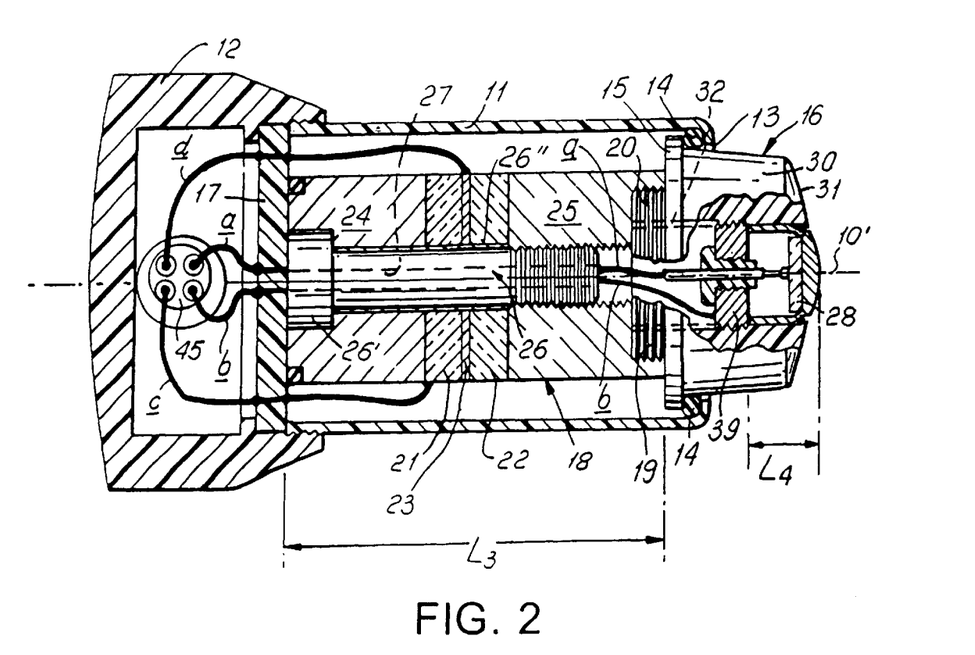
FIG. 2 is a view in longitudinal section and partly broken-away, for the device of FIG. 1.
Figures 3, 4, 5:
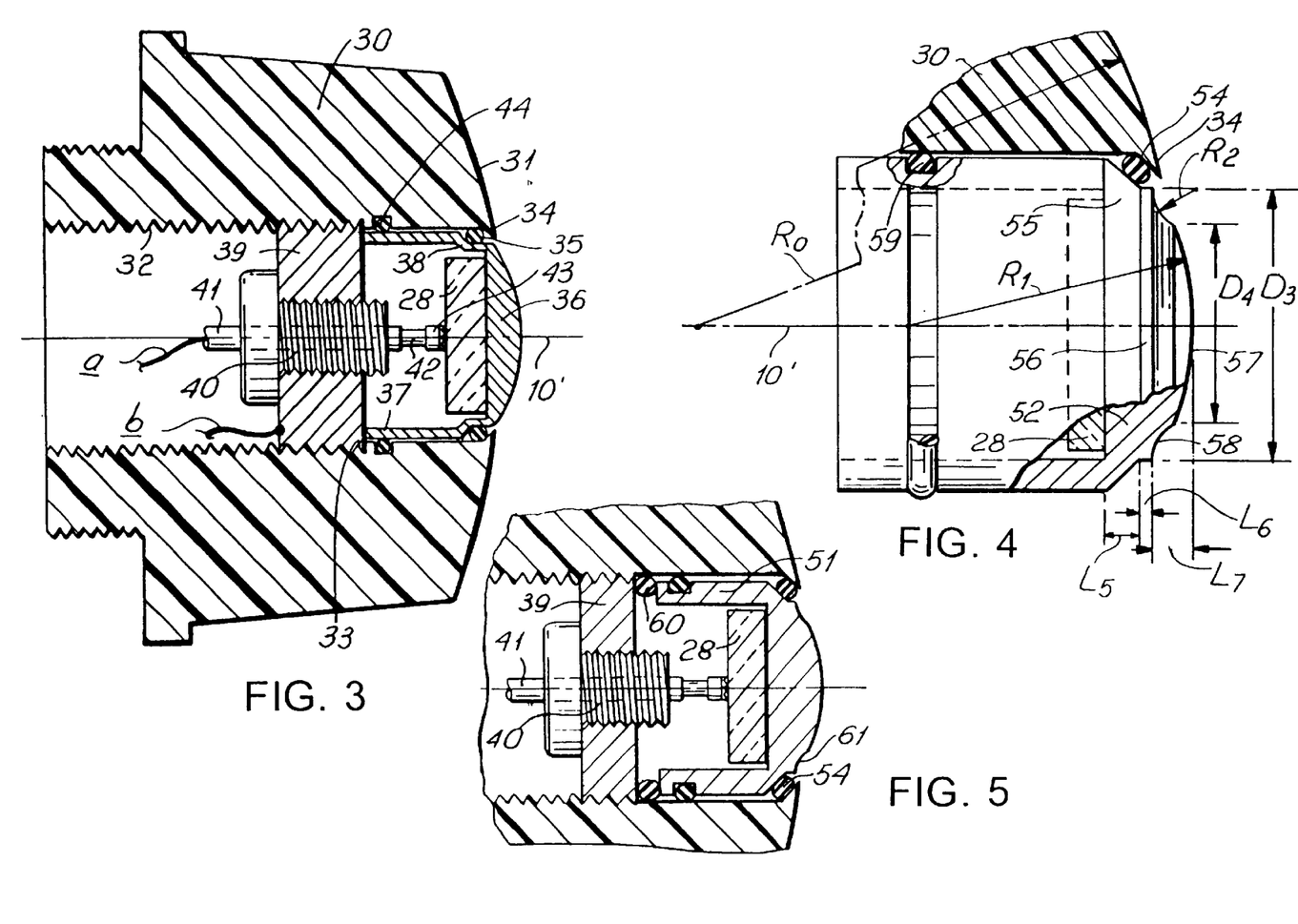
FIG. 3 is an enlarged view in longitudinal section to reveal greater detail, for the application or head end of the device of FIGS. 1 and 2.
FIG. 4 is an enlarged fragmentary view in longitudinal section, and partly broken-away, for a transducer-mounting part which is a modification of FIG. 3, but otherwise adapted for use in the device of FIGS. 1 to 2.
FIG. 5 is a view similar to FIG. 4, to show a further modification.

In FIGS. 1 to 3, the invention is shown in application to a manually manipulable device 10, which can be driven by separate ultrasonic transducers on a common central longitudinal axis 10' at each of two substantially different excitation frequencies, namely, a relatively low frequency in the range 20 to 120 kHz and a relatively high frequency in the range of 0.5 to 5 MHz. The two transducers are carried by a housing comprising an elongate barrel part 11, having removably threaded connection to a rear-closure part 12 of a handle (not otherwise shown), suitably of molded plastics material such as acetyl. At its forward or body-applicator end, the barrel part 11 is formed with a circumferentially continuous radially inward lip 13 which, via an elastomeric O-ring 14, retains a subassembly of the two ultrasonic generators and their applicator heads, the O-ring 14 being seated between lip 13 and the radially outward flange 15 of a body-applicator or head subassembly 16.

More specifically, a panel 17 of circuit-board material mounts the tail end of an elongate lower-frequency acoustic generator 18, the forward end of which has a threaded counterbore 19 to which the tail end 20 of the body-applicator subassembly 16 is securely engaged. This lower-frequency generator is shown as a longitudinally assembled sandwich, comprising two-like piezoelectric rings 21, 22 with a central conductive plate 23 therebetween; reacting masses 24, 25 are compressionally loaded by a central bolt 26 into contact with the piezoelectric rings. The head 26' of bolt 26 seats in a counterbore of the rear mass 24; the smooth cylindrical portion of its shank has running clearance with aligned central bores of piezoelectric rings 21, 22, plate 23 and the rear mass 24, being in threaded engagement at its distal end to the bore of the front mass 25; an insulating sheath 26", as of PTFE, covers the smooth-shank portion of bolt 26. Finally, bolt 26 is shown with its own central bore 27 for accommodation of excitation leads, for the high-frequency excitation of a piezoelectric element 28.

The head-end subassembly 16 comprises an annular body 30 of acetyl or other plastics material, selected for its specific impedance W closely matching that of soft tissue, as recited above. Body 30 is seen with a frusto-conical circumferential profile which converges toward the front or application end 31 which has a convex curvature of revolution about the central axis 10'. At its rear end, body 30 is characterized by radially outward flange 15 and by the reduced and externally threaded tail end 20, whereby body 30 is assembled to the threaded counterbore 19 in the front face of the front mass element 25 of the lower frequency acoustic generator 18. The bore of body 30 may be cylindrical, with internal threads 32, adapted for the suspended and substantially acoustically isolated retention of component parts (including element 28) of the high-frequency end of the device. As shown, the threads 32 extend to a shoulder 33.

Reference is now made more particularly to FIG. 3, for detail of mounting and suspension of the high-frequency piezoelectric element within the annular patient-application head or body member 30. The front end of the bore of member 30 is seen to be cylindrical, forward of shoulder 33, to the point of termination at an integrally formed radially inward lip formation 34, whereby to locate and retain an elastomeric O-ring 35. The high frequency piezoelectric element 28 is retained within the cupped closure wall of a patient-application head member 36, suitably of acoustic-grade aluminum, and provided with a preferably spherical outer contour which smoothly conforms to and effectively completes the outer contour of the front face of annular-body member 30. As shown, the head member 36 derives axially stabilized orientation from a cylindrical skirt formation 37, having running clearance with the cylindrical portion of the bore of member 30, i.e., forward of shoulder 33; and at its forward end, skirt 37 is provided with a circumferentially continuous radially inward and axially compliant integral connection 38 to the axially short portion of the cupped closure wall of head member 36. The axially compliant connection 38 is seen to provide a circumferentially continuous surface engagement to O-ring 35, in opposition to the locating lip formation 34 of member 30.

The base or open end of skirt formation 37 derives axial retention from the flat radial face of a threaded plate or mount 39 for mounting a high-frequency source connection to the back-side electrode area of piezoelectric element 28, it being understood that the front-side electrode area of element 28 has intimate electrical contact with head member 36. Preferably, the axial-reference positioning of plate 39 for skirt formation 37 is such that when plate is seated against shoulder 33, skirt 37 provides light compressionally loaded action (via connection 38) on O-ring 35. An elastomeric O-ring 44 is shown for coaxially stabilized positioning of skirt formation 37 in the bore of member 30.

For electrical supply to the back-side electrode of piezoelectric element 28, a flanged and insulating bushing 40 carries the outer tubular element 41 of a telescoping contact assembly. Bushing 40 is shown in threaded engagement with the bore of plate 39, being driven to the point of its flange engaging the axially inner face of plate 39. The contact assembly will be understood to be conventional and to include an inner spring (not shown) wherein an inner tubular element 42 is telescopically guided and urged within outer tubular element 41 to project forward along axis 10' with compressionally loaded electrical engagement of its contact foot 43 with the back-side electrode of piezo element 28.

Electrical supply to the respective high-frequency and low-frequency transducers is shown to involve separate pairs of insulated conductors within a single cable 45 having ported access to the cavity within end closure 12 and bounded by terminal board 17. For high-frequency excitation of the high-frequency transducer 28, a high-frequency source (not shown) will be understood to supply conductors a and b, shown connected to central terminals of board 17, and having insulated guidance within the bore 27 of bolt 26; conductors a and b emerge from bore 27 with an a-labeled ("hot") connection to outer tubular element 41, and with a b-labeled ("ground") connection to plate 39, it being understood that the ground connection to the high-frequency piezoelectric element is completed via the conductive property of skirt 37 and other features of head member 36, and its conductive relation to the front-side electrode of piezoelectric element 28.

In similar fashion, the second pair (c, d) of cable conductors provides supply of low-frequency excitation energy from a separate low-frequency source (not shown), to the low-frequency transducer 18. More specifically, a c-labeled ("hot") line to the back-side electrode of piezoelectric element 21 will be understood, via the conductive materials of mass 24, bolt 26, and mass 25, to apply identical low-frequency connection to the corresponding outer-electrode faces of both of the low-frequency piezoelectric elements 21, 22, while a d-labeled ("ground") connection to plate 23 completes low-frequency excitation connection to the remaining electrode areas of adjacent sides of the respective piezoelectric elements 21, 22.

The described appliance will be seen to be essentially as described for the single-applicator configuration of U.S. Pat. No. 5,549,544, involving the use of a single source of relatively low-frequency excitation, and for axially directed ultrasonic propagation from a rounded base-frontal area having a diameter of ¼ to ½ the wavelength of the relatively low frequency. This prior construction will further be seen to have now been effectively cored along the central axis, to accommodate wiring for the relatively high-frequency transducer 28, as well as its means of suspension within the bore of the low-frequency head member 30.

In FIGS. 1 and 2, symbols for length (L) and diameter (D), with identifying subscripts, have been supplied to indicate general dimensioning for the described dual-transducer, dual-frequency appliance of the invention, wherein the relatively low frequency is about 45 kHz, and wherein the relatively high frequency is about 1 MHz. The drawings of FIGS. 1 and 2 are not to scale, but illustrative general relationships derive approximately from the following:

L1=length, overall, approximately 95 mm.
L2=length of closure 12, approximately 30 mm.
L3=exposed length of barrel 11=length of low-frequency transducer, approximately 50 mm.
L4=axial length of high-frequency head member 36 (including skirt 37), approximately 12 mm.
D1=maximum handle-hub (12) diameter, approximately 55 mm.
D2=maximum diameter of low-frequency applicator head, approximately 30 mm.
D3=diameter of high-frequency applicator head, approximately 10 mm.
D4=diameter of barrel 11, approximately 40 mm.

FIG. 4 is an enlarged fragmentary sectional view of a presently preferred high-frequency body-application head configuration adapted for mounting in the bore of member 30, in place of the configuration 36 shown in FIG. 3. The high-frequency head member 50 of FIG. 4 is again cup-shaped, but having a more massive skirt formation 51 which is essentially non-compliantly integral with its closed end 52. A peripheral groove in skirt 51 retains an elastomeric O-ring 53 for centrally stabilizing action of the open end of skirt 51 in the bore of member 30. The open end of the skirt may be solidly referenced to the shoulder action of plate 39 (as in FIG. 3) or via an acoustic compliance provided by an additional elastomeric ring 54 (as is FIG. 4A). A measure of acoustic isolation is again provided by a front-end elastomeric O-ring 55 between the radially inward lip 34 of member 30 and a frustoconical section 56 which effects closure of the front end of skirt 51. The back surface of this closure is flat, with the high-frequency piezoelectric element 28 bonded thereto.

The principal point of difference for FIG. 4 resides in the body-contacting forward contouring of head member 50, in FIGS. 4 and 5. Starting from the frustoconical section or base 55, shown with an axial extent L5, a short cylindrical land (of axial extent L6) determines the effective maximum frontal area (of diameter D3) for high-frequency ultrasonic projection centered on axis 10'. And the body-contacting outer contour is the product of a presently preferred empirically determined compound surface of revolution about the central axis. This surface is described as a central outer-surface convex contour 57 which is generally spherical, with a radius R1 which is shorter than the radius $R_o$ of the outer convex surface of the low-frequency head member 30. The convex contour 57 is shown with an effective diameter D4 which is less that diameter D3, thus providing a circumferentially continuous annular region 58 that is shown to be concave, with a section radius R2 which is shorter than the convex radius R1, and which is centered at radial offset from central axis 10'. Suitably, the locus of centers for the concave section profile may be a circle of at least the diameter D3. It will be understood that, rigorously speaking, the foregoing description of the compound convex/concave body-application surface of head 52 necessarily develops a circular line of interconnection between the convex and concave components of the surface, but that a sharp line of interconnection is not desired. Therefore, it will be understood that a smoothly faired annulus of transitional inflation is preferred in the course of radial and axial development of these otherwise adjacent convex and concave surface profiles.

The embodiment of FIG. 5 will be understood to be in most respects as described for FIG. 4. The principal difference resides in the provision of an additional axially compliant ring 60 of electrically conductive material, for example, an elastomeric O-ring which has been silver-coated. Thus, in FIG. 5, the body-application head 61, with its high-frequency piezoelectric element 28, is axially compliantly retained in residually compressed and axially pre-loading relation to similar but opposing compression of the front-end O-ring, thus achieving a measure of acoustic isolation between the respective low-frequency and high-frequency ultrasonic operations of the overall device.

Figure 6A:
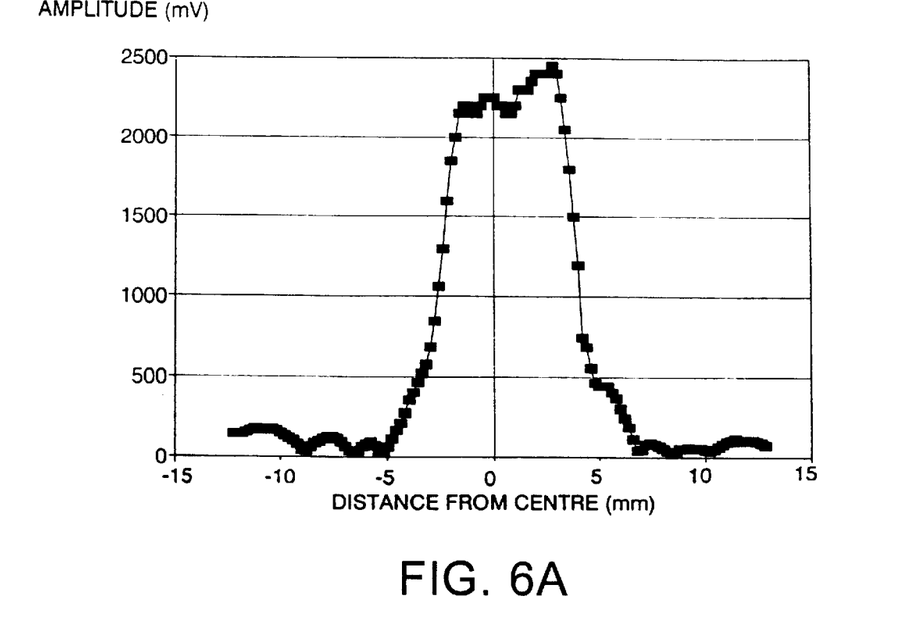
FIG. 6A is a graph to show a beam profile generated by a device of the invention.
Figure 6B:
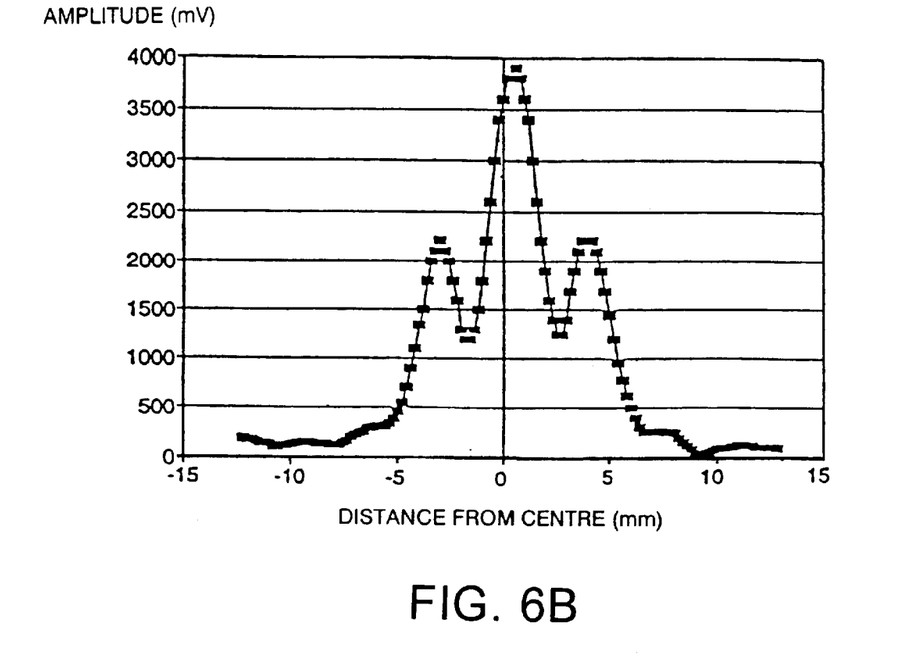
FIG. 6B is a similar graph to show a beam profile which is not satisfactory.

The convex/concave body-application surface contour of FIGS. 4 and 5 is a product of empirical development for a variety of body-contact surface configurations, wherein various specimen configurations were subject to field-measurement in water, at the same predetermined level of energy supplied to the transducer. Field measurements were made via a small (effectively 1-mm diameter) hydrophone that is manipulable in a volume of water into which the sealed front face of the described device is immersed and directed, with excitation at high frequency (about 1 MHz). Measurements were made for a series of discrete positions to both sides of the central axis 10', on a single transverse path of traverse across the field of high-frequency ultrasonic propagation. The plot of FIG. 6A is illustrative of the measured response pattern for the front-surface configuration of FIGS. 4 and 5 and is interpreted to demonstrate a relatively uniform response within the relatively narrow range of ±5 mm for portions of field measurements at opposite offsets from the central axis 10', it being recalled that the effective diameter D3 of the high-frequency radiating surface is about 10 mm. By contrast, using the high-frequency element with an essentially flat application head, one obtains a field response as in FIG. 6B, wherein a central spike in the response is not only of excessive and unacceptable magnitude, virtually 3900 millivolts on-axis, and dropping to 1200 millivolts before rising to symmetrical secondary peaks of 2200 millivolts, all within the same ±5 mm region for the response pattern of FIG. 6A. The spike of FIG. 6B will be understood to be unacceptable because it represents, in application to living tissue, a grossly elevated locale of potential tissue damage, with relatively little prospect of therapeutic benefit to surrounding tissue within the involved 10-mm diameter of propagation.

In the case of the high-frequency head profiling of FIGS. 4 and 5, wherein the radiating-face diameter D3 is 10 mm, other significant dimensions are, illustratively:

Outer convex radius R1, in the range 20 to 30 mm.
Annulus 58, concave radius R2, in the range 2 to 2.5 mm.
Axial length of conical frustum (55) L5, about 1.5 mm.
Axial length of land (56) $L_6$, about 1.0 mm.
Axial extent of radiating face (57, 58) $L_7$, about 1.4 mm.

EXAMPLES

Performance testing was carried out on a prototype Ultrasound Diathermy Device which addressed the heating ability at depth in a phantom.

| Low-Frequency Characteristics | |
| --- | --- |
| Frequency | 45 kHz ± 5% |
| ERA | 13.5 cm$^2$ |
| BNR | 6.5 |
| Beam Type | Diverging |
| Power Settings | 0.4 W, 0.6 W, 1 W |
| Mode | Continuous |

| High-Frequency Characteristics | |
| --- | --- |
| Frequency | 1 MHz ± 5% |
| ERA | 0.9 cm$^2$ |
| BNR | <5.0 |
| Beam Type | Diverging |
| Power Settings | 0.5 W, 1 W, 2 W |
| Mode | Continuous and Pulsed (20% duty cycle) |

General

The timer has an accuracy for different settings of:

| | |
| --- | --- |
| Less than 5 minutes | ± 1.7% |
| 5–10 minutes | ± 0.7% |
| Greater than 10 minutes | ± 0.5% |

The maximum timer setting is 30 minutes.

NOTE: The Beam Non-Uniformity (BNR) is a measure of the variation in power density across the effective radiating area of the applicator. The unique coaxial design of the device was evolved by independent measurement of each transmitting source.

Diathermy Effects

Figure 7:
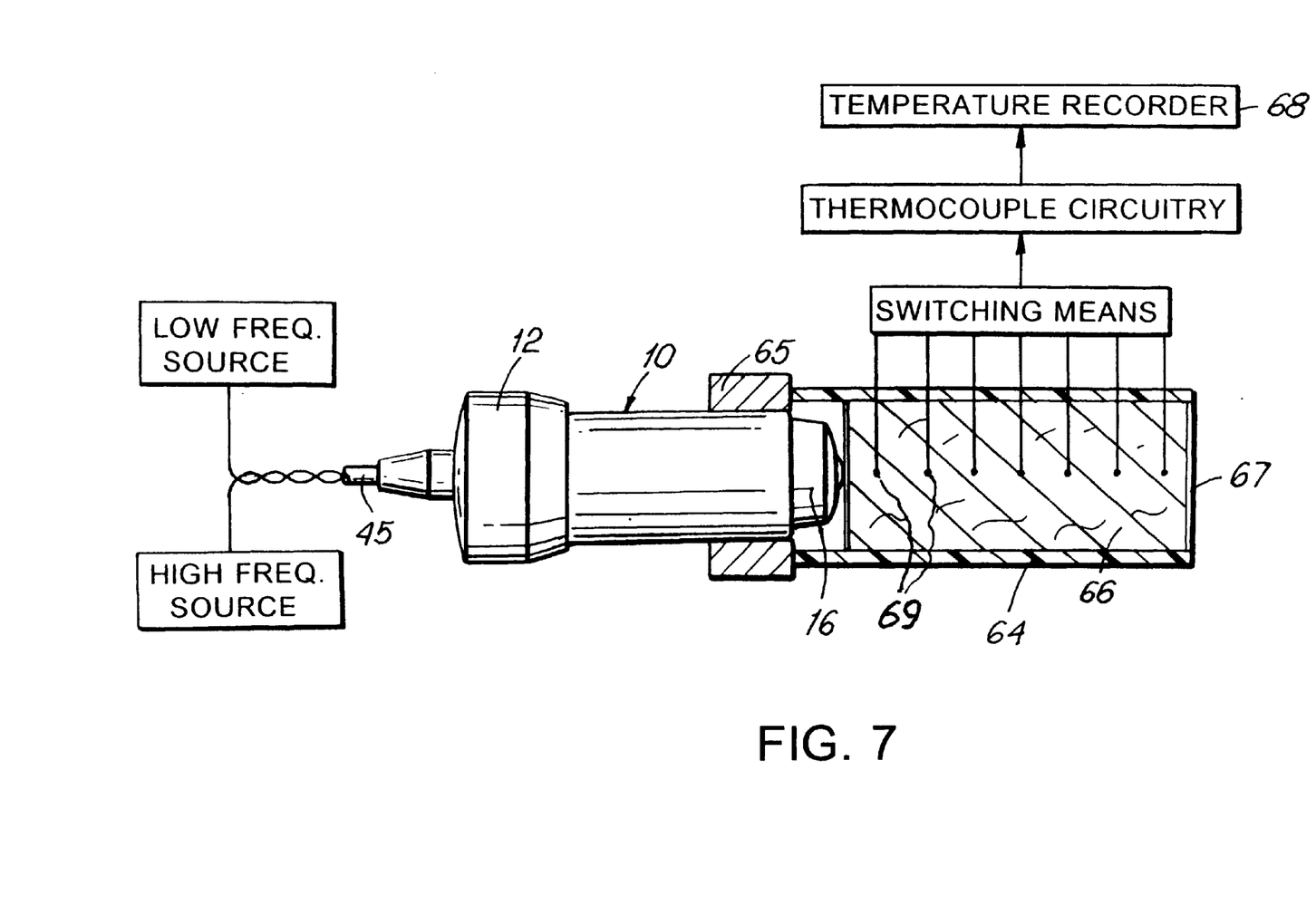
FIG. 7 is a schematic diagram of test apparatus to measure heat development in porcine tissue, using a device of the invention.

The apparatus shown in FIG. 7 was used experimentally to examine the heat development in porcine muscle of ultrasonic vibration at 45 kHz via the low-frequency transducer 18 and at 1 MHz via the high-frequency transducer 28. A container 64 is held to an ultrasound handset 10 by an adaptor 65. Within the container 64 is a transmission medium 66 comprising de-gassed water, castor oil and porcine muscle tissue, sealed by membrane 67 at a remote end of the container. A temperature recorder 68 keeps a record of the temperatures measured by thermocouples 69 at various axial distances from the head 16.

Figure 8:
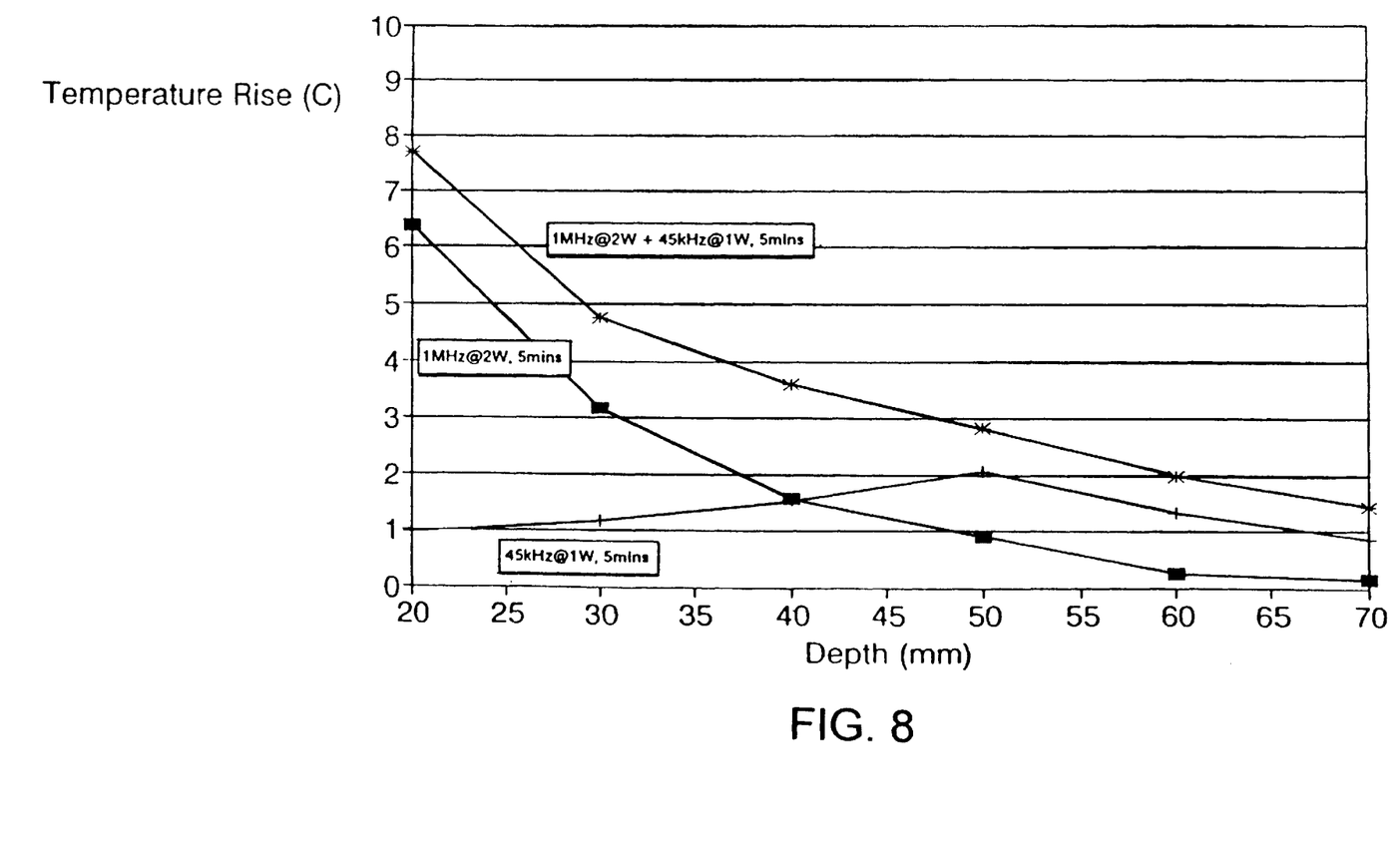
FIG. 8 is a set of three graphs of measured temperature rise as a function of penetration depth as measured in the test apparatus of FIG. 7; these graphs show, for a single 5-minute application time, the separate penetration-depth of heat development for ultrasonic radiation at each of two different frequencies, alongside the corresponding penetration-depth of heat development for the concurrent use of both frequencies.

Referring now to FIG. 8, tests for heating-ability on phantoms were carried out for the device and for a comparative device, with a 1-cm applicator. All the graphs are plotted according to an average of three runs to show the temperature rise at depths in pig muscle. These tests demonstrate that the device embodying the invention operating at a maximum output provides equal or better heating characteristics than the Mettler 720 at maximum output at all depths measured. The statement that the device has equal or better heating characteristics does not mean that more heat is deposited at all depths than the Mettler, because the Mettler definitely causes more surface heating than the device of the invention. However, surface heating is an unwanted side effect in diathermy as it tends to limit the amount of heating at depth that can be achieved because of the limits of patient tolerance of surface heating.

First, the device was evaluated under three conditions in a phantom containing pig muscle:

(1) 45 kHz alone @ 1W
(2) 1 MHz alone @ 2W
(3) 45 kHz @ 1W plus 1 MHz @ 2W (simultaneously)

The results, shown in FIG. 8, demonstrate the advantages of dual frequency treatments. Note that while the treatment at 1 MHz alone deposits six times the energy of the 45 kHz treatment at 2 cm depth (three times, on a per watt basis), deeper in the phantom at 5 cm depth, the 45 kHz treatment actually deposits twice the energy of the 1 MHz treatment, in spite of having only half the output power. As can be readily seen from the graphs, the energy deposited at depth by the 45 kHz component is obtained at a small cost in surface heating. This results in much better heating performance for the dual frequency treatment beyond 4 cm depth than can be obtained with the 1-MHz component alone.

The device with only the 1 MHz channel activated (at 2W) provides heating profiles that are similar to those of a conventional device (one operating at 1 MHz operating at 2W, which can be compared with the device at 1 MHz alone (also at 2W) in FIG. 8. Note that the heating pattern at depth is qualitatively similar for the two devices, though because of differences in beam divergence characteristics, they are not identical.

The dual-frequency treatment heating performance of the device at maximum output may be compared directly with a conventional 1 MHz device operating at 2 W (its maximum). While the heating caused by the two devices is similar at 3 cm depth, the device embodying the invention produces three times the heating at 5-cm depth than does the conventional device. It is noted that the increased penetration of energy is obtained at less "cost" in surface heating.

These data demonstrate that the device has heating characteristics that are equal to or better than those of a conventional device with 1-cm applicator.

What is claimed is:

1. A non-invasive dual-frequency body-applicator therapeutic device, comprising first and second ultrasonic piezoelectric transducers on a single axis of longitudinal acoustic propagation, the first transducer including at one longitudinal end a generally cylindrically annular body-application head having a cylindrical bore on said axis, said first transducer having means for independent connection to a first source of ultrasonic acoustic-signal excitation at a first frequency within the range 10 kHz and 4 MHz; said second transducer having means for independent connection to a second source of ultrasonic acoustic-signal excitation at a second frequency within said range and being mounted in said bore with at least some acoustic isolation from said first transducer, and having at said longitudinal end a body-application head; said first frequency being lower than said second frequency, and said annular body-application head having a body surface-active engagement face of a material having impedance-matching properties with respect to engaged regions of a body-tissue area contacted by the impedance-matching active-engagement face of said annular body-application head.

2. The device of claim 1, in which the body-application longitudinal ends of said heads are concentrically adjacent in substantially the same geometric radial plane about said axis.

3. The device of claim 1, in which the body-application end of said annular head is convexly contoured as a surface of revolution about said axis.

4. The device of claim 3, in which the convex contour of said annular head is generally spherical.

5. The device of claim 4, in which the body-application end of said second-transducer head is generally spherical and is centered on said axis.

6. The device of claim 5, in which the body-application end of said second-transducer head is generally spherical but of spherical radius less than that of said annular head.

7. The device of claim 4, in which the body-application end of said second-transducer head comprises a central convex generally spherical portion centered on said axis and an annular concave surface of revolution contiguous to said central convex generally spherical portion.

8. The device of claim 7, in which said annular concave surface of revolution is based on a section profile wherein the convex-surface portion is based on a first substantially circular arc centered on said single axis, and in which the annular concave-surface portion is based on a substantially circular second arc of shorter radius than said first arc and centered at radial offset from said single axis.

9. The device of claim 8, in which the body-application end of said second-transducer head is characterized by a circumferentially continuous and smoothly faired transitional connecting region of inflexion between said convex and concave surface portions.

10. The device of claim 1, in which the body-application head for said second transducer is generally cup-shaped, with a cylindrically annular skirt portion having an open tail end and integrally formed with a closed head-end portion, the cylindrical bore of said annular body-application head having a radially inward shoulder for axially positional referencing of the open end of said skirt portion, said head-end portion having a convex body-application outer surface and a flat inner surface, said second transducer having a flat radiating face in adhesively bonded relation to the flat inner surface of said closed head-end portion.

11. The device of claim 10, in which an elastomeric O-ring is axially-interposed between coacting axially spaced confronting formations of said annular body-application head and of the body-application head for said second transducer, whereby said O-ring can provide at least some acoustic isolation of said head ends with respect to each other.

12. The device of claim 10, in which a circumferentially continuous annular frustoconical portion of the body-application head for said second transducer head integrally and axially compliantly connects said skirt portion to said closed head-end portion, whereby said frustoconical portion can provide at least some acoustic isolation of said head ends with respect to each other.

13. The device of claim 10, in which an annular member of elastomeric material is axially interposed between said shoulder and the open end of said skirt portion, whereby said annular member of elastomeric material can provide at least some acoustic isolation of said head ends with respect to each other.

14. The device of claim 10, in which said skirt portion has running clearance with the bore of said generally cylindrically annular body member, and means including an elastomeric O-ring interposed between said bore and said skirt portion for radially stabilized positioning of said skirt portion with respect to said bore.

15. The device of claim 5, (a) in which said annular body-application head includes a circumferentially continuous radially inwardly extending lip formation at said one longitudinal end of said bore, (b) in which said bore is internally threaded near the other longitudinal end thereof, (c) in which circumferentially continuous externally threaded means engaged to the bore threads defines a radially inward shoulder formation at axial offset from said lip formation, (d) in which the body-application head of said second transducer includes a cylindrically annular portion having running fit in said bore-between said lip and shoulder formations, (e) a first annular elastomeric ring retained between said lip formation and the cylindrically annular portion of the second-transducer head, and (f) a second annular elastomeric ring retained between said shoulder formation and the cylindrically annular portion of the second-transducer head.

16. The device of claim 15, in which each of said elastomeric rings is an O-ring.

17. The device of claim 1, in which the body-application head of said second transducer includes a patient-application member of acoustic-grade aluminum.

18. The device of claim 17, in which said patient-application member of said second transducer has an outer body-contact face in substantial longitudinal register with the front-end profile of said body-application head.

19. Apparatus for non-invasive ultrasonic therapeutic treatment via a surface portion of a living body, wherein the apparatus comprises piezoelectric means to generate ultrasonic energy, said piezoelectric means comprising a first generator means and a second generator means, said first generator means for delivery of energy at a first frequency within the range 10 kHz and 4 MHz and generally along a longitudinal axis, second generator means for delivery of energy at a second frequency within said range and generally along said longitudinal axis, said first frequency being lower than said second frequency; a first body-application head associated with said first generator means for first-frequency ultrasonic action on a first region of said surface portion, and a second body-application head carried by said first body-application head and associated with said second generator means for second-frequency ultrasonic action on a second region of said surface portion.

20. An apparatus as claimed in claim 19, wherein said first generator means generates energy at a frequency in the range between 10 and 110 kHz, advantageously 20 to 100 kHz, and optionally in the region of 45 kHz.

21. An apparatus as claimed in claim 20, wherein said second generator means generates energy at a frequency in the range between 0.5 and 4 MHz, advantageously 0.5 to 3 MHz, and optionally in the region of 1 MHz.

22. The apparatus of claim 19, in which said first body-application head is of a dense-polymer material selected from the group consisting of acetyl, polypropylene and polycarbonate.

23. The apparatus of claim 19, in which said first body-application head is of a plastics material having a specific impedance (W) in closely matching relation to that of human soft tissue.

24. A non-invasive dual-frequency body-applicator therapeutic device, comprising first and second ultrasonic piezoelectric transducers on a single axis of longitudinal acoustic propagation, the first transducer including at one longitudinal end a generally cylindrically annular body-application head having a cylindrical bore on said axis, said first transducer having means for independent connection to a first source of ultrasonic acoustic-signal excitation within the range 10 kHz and 4 MHz; said second transducer having means for independent connection to a second source of ultrasonic acoustic-signal excitation at a second frequency within said range and including at said one longitudinal end a body-application head carried within said bore, and said first source of acoustic-signal excitation being at a lower frequency than that of said second source.

* * * * *